United States Patent [19]

Silhavy et al.

[11] 4,336,336

[45] Jun. 22, 1982

[54] FUSED GENE AND METHOD OF MAKING AND USING SAME

[75] Inventors: Thomas J. Silhavy, Wollaston; Howard A. Shuman, Brookline; Jon Beckwith, Cambridge, all of Mass.; Maxime Schwartz, Paris, France

[73] Assignee: President and Fellows of Harvard College, Cambridge, Mass.

[21] Appl. No.: 3,082

[22] Filed: Jan. 12, 1979

[51] Int. Cl.$^3$ ............................................. C12N 15/00
[52] U.S. Cl. ..................... 435/172; 435/91; 435/68; 435/207; 536/27
[58] Field of Search .................... 435/172, 91; 536/27

[56] References Cited

PUBLICATIONS

Hofnung, Genetics, vol. 76, pp. 169–184, (1974).
Hofnung, Mol. Gen. Genet., vol. 112, pp. 117–132, (1971).
Silhavy et al., Proc. Nat. Acad. Sci., vol. 73, No. 10, pp. 3423–3427, (1976).
Villa-Komaroff et al, Proc. Nat. Acad. Sci., vol. 75, No. 8, pp. 3727–3731, (Aug. 1978).
Casadaban, J. Mol. Biol. 104, pp. 541–555, (1976).
Randall-Hazelbauer et al., J. Bact., vol. 116, pp. 1436–1446, (1973).

*Primary Examiner*—Alvin E. Tanenholtz

[57] ABSTRACT

This invention is a method for fusing, within a bacterial host, a gene for a cytoplasmic protein to a gene for a non-cytoplasmic protein, so that the hybrid protein produced is transported to, near, or beyond the cell surface for ease of collection and purification, or for immunological use. The invention also encompasses the fused gene created by the disclosed method.

19 Claims, 5 Drawing Figures

FUSED GENE AND METHOD OF MAKING AND USING SAME

The invention described herein was made in the course of work under grants from National Science Foundation (PCM76-21955), American Cancer Society (VC-13F), Delegation General a la Recherche Scientifigue et Technique (75 7 0039), Jane Coffin Childs Memorial Fund For Medical Research (61-431), National Research Service Award (5T32GMO7306-02), National Institute of General Medical Sciences (1 ROI GM 25524-01) and Centre National de la Recherche Scientifigue (CNRS) of France and Institut Pasteur, Paris, France.

This invention relates to a method for fusing a bacterial gene which codes for a bacterial cytoplasmic protein to the non-cytoplasmic directing portion of a gene which codes for a non-cytoplasmic protein, that is, a protein which is normally transported to the bacterial outer membrane, the periplasmic space between the cytoplasmic and outer membranes, or outside the bacterial cell, so that a hydrid protein is produced. The cytoplasmic protein fused to the non-cytoplasmic carrier protein is thereby transported to, or beyond the cell surface, or to the periplasmic space, thus facilitating its collection and purification, or enabling the bacteria to be used as an immunogen. After the gene fusion described herein is accomplished, the fused gene can be isolated and a gene coding for any protein can be inserted into it using conventional techniques. This fused gene can then be used to infect, transform, or transduce other bacterial cultures, so that they will produce hybrid proteins which are carried to the cell surface.

Two bacterial genes for cytoplasmic proteins have been fused, Casababan, J. Mol. Biol. (1976) 104:541 and a gene for a cytoplasmic protein has been fused to a gene for a protein which travels to the inside of the inner cytoplasmic membrane, Silhavy et al., Proc. Natl. Acad. Sci. (1976) 73:3423. However, neither method is useful for purification or collection of a cytoplasmic protein or for the creation of immunologically-effective bacteria, since in both methods the hybrid protein remains in the cytoplasm.

The present invention can be applied to any bacteria including the gram positive bacteria, whose excreted proteins can act as carriers, and, even more usefully, to the gram negative bacteria, whose cell surface and periplasmic space proteins can act as carriers.

The genes which produce the non-cytoplasmic carrier proteins can include any genes which code for proteins which travel to the periplasmic space or the cell surface or which are excreted by the cell.

The genes which code for the cytoplasmic proteins include any genes for cytoplasmic proteins which can be fused to genes for carrier proteins, and which themselves produce useful proteins, or into which can be inserted, by conventional methods, genes coding for useful proteins. These useful proteins include eukaryotic cell proteins such as insulin, peptide hormones such as somatostatin, and specific viral and bacterial antigens.

When ordinarily produced in $E.$ $coli$, for example, the cytoplasmic and useful proteins previously mentioned remain in the bacterial cytoplasm, making purification from the bulk of $E.$ $coli$ proteins a difficult problem. Also, the useful foreign proteins can be degraded by proteases in the cytoplasm, so that they may not be recovered at all. However, if a gene coding for a useful protein is inserted into the gene for a cytoplasmic protein, after the gene for the cytoplasmic protein has been fused to a gene coding for a carrier protein according to the method of the present invention, collection and purification can be greatly facilitated, and the degradation problem can be diminished as well.

The present invention has addditional advantages when the useful protein is a bacterial or viral antigen normally produced by a pathogenic organism. For example, if the host bacterium is $E.$ $coli$, when the gene for the antigen of a pathogen is inserted into the gene for a cytoplasmic protein which has been fused to the gene for a carrier protein according to the method of the present invention, there is produced a hybrid protein, part of which is the pathogenic antigen, which can be transported to the cell surface. The whole killed $E.$ $coli$ can thus be used as an immunogen; the need for purification is eliminated. Also, the immunological effectiveness of these cells is likely to be greater than that of purified antigen because insoluble antigens are generally more effective than soluble ones.

The pathogenic antigens on the $E.$ $coli$ cell surface can be particularly useful in localized immunization against diarrhetic diseases of the lower gut. The only protective immunity to these diseases is mediated by secretory antibodies ($Ig^A$) produced in the vicinity of the lower gut. Administration of soluble antigens is ineffective in eliciting the appropriate secretory antibody response, but oral administration of killed $E.$ $coli$ with the antigen on the cell surface can be effective. $E.$ $coli$ is a natural inhabitant of the gut and is itself not harmful; neither is the surface antigen from the pathogen itself pathogenic. The $E.$ $coli$ with the surface antigen would, however, elicit the appropriate protective localized secretory antibody response.

It can be seen that the fused gene, even without another gene inserted into it, is itself useful in three ways, implicit in the aforementioned description: First, the bacterial cytoplasmic protein coded for may itself be a useful protein and therefore advantageously exported to the bacterial cell surface. Second, the fused gene is the vehicle into which a gene for any other useful protein which is advantageously exported is inserted. Third, the isolated fusion, which is sometimes incorporated into a phage, can be used to infect, transform, or transduce other cultures.

Figure 1:
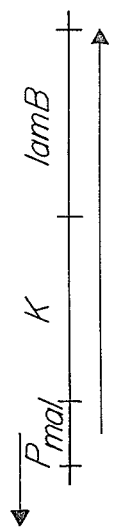
FIG. 1 shows the section of the $E.$ $coli$ chromosome containing the lamB gene, which codes for a carrier protein.
Figure 3:
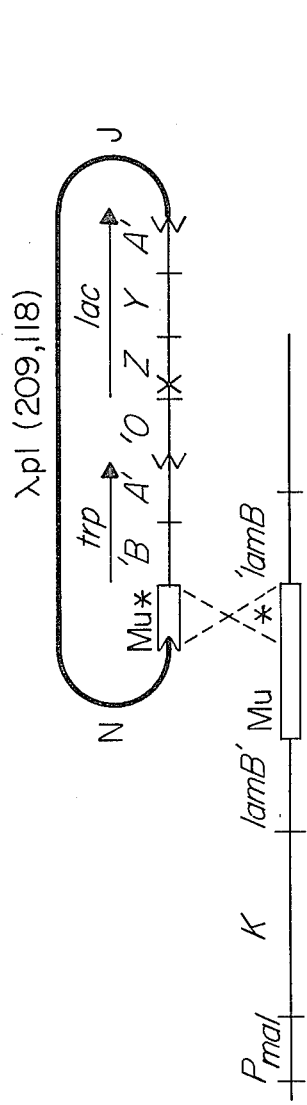
FIG. 3 shows a λ phage, containing a lacZ gene, which codes for a cytoplasmic protein, β-galactosidase, and the site at which the λ phage is inserted into the lamB region of the $E.$ $coli$ chromosome.

In FIGS. 1 and 3, arrows indicate direction of transcription.

Figure 4:
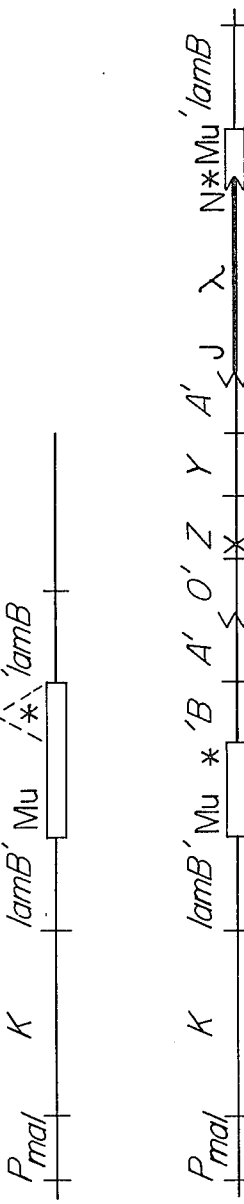

FIG. 4 shows the $E.$ $coli$ chromosome immediately after the insertion of the λ phage.

Figure 5:
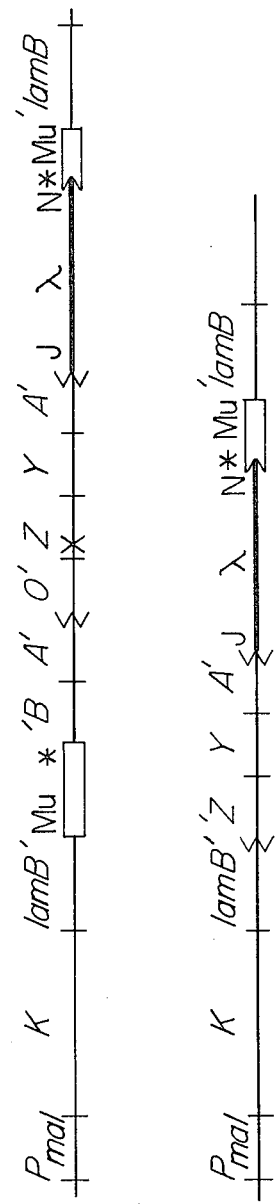

FIG. 5 shows the $E.$ $coli$ chromosome after a Mu phage and a part of the lamB gene have been spontaneously deleted.

The following specific example is intended to illustrate more fully the nature of the present invention without acting as a limitation upon its scope.

EXAMPLE

The carrier protein employed is a cell surface protein called λ (lambda) receptor, which is coded for by the *E. coli* lamB gene. This protein serves as the receptor for the bacterial virus (phage) λ.

The host organism of this example is an MC4100 strain of *E. coli* whose chromosome lacks the gene coding for the cytoplasmic protein β-galactosidase (the lacZ gene) and also lacks a λ phage. These bacteria are referred to as lac-delete non-λ lysogens.

The transported protein in this example, β-galactosidase, is normally found in the bacterial cytoplasm. However, when the hybrid β-galactosidase-λ receptor protein is produced from the fused lacZ-lamB gene using the method herein described, β-galactosidase, attached to λ receptor, is carried to the cell surface. Fusions produced using the method described herein can be divided into five classes, according to the amount of lamB gene present. Classes containing a substantial portion of the lamB gene, including the non-cytoplasmic-directing region, have molecular weights of approximately 141,000 daltons, and are designated class IV and class V fusions. These fusions are deemed more desirable for the purposes stated than are the class I, II, and III fusions, which contain a smaller portion of the lamB gene, and have molecular weights of between 116,000 and 137,000 daltons. The hybrid proteins produced by all classes of fusions contain an $NH_2$-terminus coded for by the lamB retion of the fused gene.

Figure 2:
FIG. 2 shows the lamB gene after a Mu phage has been inserted into it.

The first step of the method described creates and selects the $Mu_{cts}$-induced lamB mutants shown in FIG. 2, so that there will be homology between the lamB region of the *E. coli* chromosome and the λ phage containing the lacZ gene. Ten spots of the $mu_{cts}$ lysate are deposited on a lawn of lac-delete, non-λ lysogenic *E. coli*, strain MC4100. After an overnight incubation at 30° C., a loopful from each spot is inoculated into 5 ml of TYE and the cultures are grown to exponential phase at 30° C. The cultures are then centrifuged and the cells resuspended in $10^{-2}$ M $MgSO_4$ at a density of about $5 \times 10^8$ cells/ml.

To select the Mu insertions in the lamB region, and eliminate Mu insertions in other regions, a 0.2 ml sample of each suspension (i.e., $10^8$ cells) is mixed with 0.1 ml of a λV stock titering $8 \times 10^{10}$ pfu/ml. After 20 min. at room temperature, one milliter of TYE is added and the cultures are incubated for 2 hours at 30° C. Samples of the cultures are then streaked on TTZ maltose plates covered with $10^{10}$ λV pfu. Two Mal+ colonies are kept from each culture. The mutants from the ten different cultures are necessarily independent. The two mutants obtained from the same culture are almost certainly also different from one another (Indeed when two Mal colonies were isolated from the same cultures, in 8 cases out of 10 they turned out to be in different genes (malT and malK) and therefore obviously different).

The second step of the method involves insertion of the lambdoid phage shown in FIG. 3, λ p1 (209, 118), containing the lacZ gene, into the *E. coli* lamB gene region. The λ p1 (209, 118) phage can be obtained using the method described in Casadaban, J. Mol. Biol. (1976) 104:541. Since this phage does not adsorb to the lamB mutants, a phenotypically-mixed lysate must be prepared so the phage may be injected into the bacterial cell. This is done as follows: *E. coli* strain MC4100 are grown exponentially in TYE to a density of $10^9$ cells/ml. The cells are centrifuged, and resuspended in $10^{-2}$ M $MgSO_4$ at $5 \times 10^9$ cells/ml. To 0.2 ml of this suspension are added 0.3 ml of a λP1 (209, 118) stock titering $10^{10}$ pfu/ml, and 0.3 ml of a λcIh$_{80}$attΔ titering $9 \times 10^{10}$ pfu/ml. (The m.o.i. of each phage is therefore about 3.) After 20 min. at room temperature, 5 ml of TYE is added and the culture is incubated at 37°. After 2 hours $CHCl_3$ is added, the suspension is centrifuged and the supernatant is titered. It contains about $4 \times 10^9$ λcIh$_{80}$attΔ pfu/ml and $2 \times 10^9$ λP1 (209,118) pfu/ml. Overnight cultures of the mu lysogens are centrifuged, and resuspended in $10^{-2}$ M $MgSO_4$, at $2 \times 10^9$ cells/ml. Then 0.1 ml of the suspensions is incubated with 0.1 ml of the above lysate for 45 min. at 30° C.

The third step of the method, selecting the λ p1 (209, 118) lysogens, is accomplishing by streaking samples (with a loop) on TYE plates coated with about $10^9$ λcIH$_{80}$attΔ particles. After 24 hours at 30° C., colonies are streaked against λcIH$_{80}$ and φ 80 vir. Between 10 and 60% of the colonies turn out to be the desired lysogens shown in FIG. 4.

The fourth step, selection of the lysogens which, by spontaneous deletion of part of the λ P1 (209,118) phage, a Mu phage, and part of the lamB gene, have become the desired lamB-lacZ fusions shown in FIG. 5, is accomplished according to the following method: the lysogens are grown overnight in LB. Fresh cultures are then centrifuged and approximately $5 \times 10^9$–$10^{10}$ cells are then plated in M63 lactose agar at 42°. After 24 hours of incubation, the selection media is shifted to 37°. Media is left at this temperature until colonies appear. In some cases 30–40 days is required. A Lac+ thermoresistant clone is classified as a lamB-lacZ fusion strain when its β-galactosidase is maltose-inducible.

The lamB-lacZ fusion strains in classes IV and V produce large amounts of hybrid protein, part of which is β-galactosidase, and all or most of which is transported to the cell surface. The presence of β-galactosidase at the cell surface can be demonstrated using any of three methods (these methods also detect β-galactosidase, in lower amounts, at the cell surface in class III fusions):

(i) Using mutants lacking lactose transport systems, it can be shown that the fusions can grow on lactose even in the absence of a lactose transport system. This result indicates the presence of β-galactosidase activity outside of the cytoplasmic membrane barrier.

(ii) Biochemically, using sucrose density gradients, the presence of β-galactosidase activity in an outer membrane fraction can be shown.

(iii) Using conventional techniques, the outer membrane fraction can be isolated and electrophoresis, employing polyacrylamide gels, can be used to separate out and identify the hybride β-galactosidase.

If the lamB-lacZ fusions are to be used to transduce other cultures, or if a gene for a useful protein such as somatostatin is to be inserted into the fused gene, the fused gene, and the phage of which it is a part, are isolated according to the following technique. Fresh colonies of fusion strains are stabbed into TYE agar which had previously been layed with 2.5 ml of H-Top agar containing 0.1 ml of a stationary phase culture of the indicator strain MC4100. By using a grid, as many as 50 fusion colonies can be stabbed into one TYE plate.

The plates are then placed under a UV lamp for 50 seconds, or the time required to kill 50% of the cells. The plates are then incubated for approximately 6 hours in the dark, or until visible lysis is detected around each stab. Patches from each zone of lysis are then streaked onto maltose agar, containing XG, which had been spread with 0.2 ml of a stationary phase culture of MC4100. Dark blue plaques are purified several times by restreaking on the same media.

Isolated dark blue plaques are then collected by stabbing into the agar with a pasteur pipette. Each small cylindrical piece of agar with the plaque on top is then transfersed to 0.2 ml of a stationary phase culture of MC4100. After phage adsorption has occurred for 10 minutes at room temperature, 2.5 ml of H-Top is added and the suspension is poured onto TYE agar. When lysis is nearly confluent, 4 ml of LB broth is added and Top agar layer is scraped from the plate. The lysates are then treated with several drops of chloroform, vortexed, and centrifuged for clarification. From a single plaque approximately 5 ml of lysate with a titer of $5 \times 10^{10}$ plaque-forming units/ml is generally obtained.

The lysate can now be used to infect other bacterial cultures, so that the phage, including the fused gene, is incorporated into the bacterial chromosome. This is done using conventional techniques such as those described in J. Miller, Experiments in Molecular Genetics, Cold Spring Harbor Laboratory, Cold Spring Harbor, N.Y. 1972.

Alternatively, the lysate can now serve as a vehicle for the insertion of any gene for a useful protein into the fused genes. Then, using the aforementioned conventional techniques, the fused genes containing the insertions can be used to infect other cultures. The insertion of a gene for any useful protein into the fused genes is accomplished using conventional techniques such as that described in Itakura et al., Science (1977) 198:1056.

What is claimed is:

1. A fused gene which comprises a bacterial gene coding for a cytoplasmic protein fused to the non-cytoplasmic directing region of a gene coding for a non-cytoplasmic protein which is normally transported to or beyond the cell surface, such fused gene being capable of coding for a hybrid protein which is transported beyond the periplasmic space and either to the cell surface, or beyond the cell surface, of a bacterial host.

2. The fused gene of claim 1, further comprising a gene coding for a eukaryotic cell protein inserted into said fused gene.

3. The fused gene of claim 1, further comprising a gene coding for a viral protein inserted into said fused gene.

4. The fused gene of claim 1, further comprising a gene coding for a bacterial protein inserted into said fused gene.

5. A method for making the fused gene of claim 1 which comprises, within a host bacterium, fusing to a gene coding for said cytoplasmic protein the non-cytoplasmic-directing region of a gene coding for a non-cytoplasmic protein, and selecting the bacteria containing the fused gene.

6. The method as claimed in claim 5, which further comprises the step of inserting into said fused gene the gene coding for a eukaryotic cell protein.

7. The method as claimed in claim 5, which further comprises the step of inserting into said fused gene the gene coding for a viral protein.

8. The method as claimed in claim 5, which further comprises the step of inserting into said fused gene the gene coding for a bacterial protein.

9. The method as claimed in any of claims 5 to 8 in which said host bacterium is any of the gram negative bacteria.

10. The method as claimed in any of claims 5 to 8 in which said host bacterium is any of the gram positive bacteria.

11. The method as claimed in any of claims 5 to 8 in which said gene coding for said cytoplasmic protein is part of a phage which is inserted into the host bacterial chromosome to create the fusion.

12. The method as claimed in any of claims 5 to 8 in which said gene for said cytoplasmic protein is the gene for $\beta$-galactosidase.

13. The method as claimed in claim 9 in which said gene for said cytoplasmic protein is the gene for $\beta$-galactosidase.

14. The method as claimed in claim 10 in which said gene for said cytoplasmic protein is the gene for $\beta$-galactosidase.

15. The method as claimed in any of claims 5 to 8 in which said gene coding for said non-cytoplasmic protein is the gene for $\lambda$-receptor.

16. The method as claimed in claim 11 in which said phage is a lambdoid phage.

17. The method as claimed in claim 16 in which said lambdoid phage is $\lambda$ P1 (209,118).

18. The method as claimed in claim 11 in which said gene for said cytoplasmic protein is the gene for $\beta$-galactosidase.

19. The method as claimed in claim 16 or 17 in which said gene for said cytoplasmic protein is the gene for $\beta$-galactosidase.

* * * * *